United States Patent
Fremuth et al.

(10) Patent No.: US 10,852,226 B2
(45) Date of Patent: Dec. 1, 2020

(54) APPARATUS AND METHOD FOR DETERMINING THE MOISTURE OF A SAMPLE

(71) Applicant: BRABENDER MESSTECHNIK GMBH & CO. KG, Duisburg (DE)

(72) Inventors: Kay Fremuth, Duisburg (DE); Tobias Nabbefeld, Sonsbeck (DE)

(73) Assignee: Brabender Messtechnik GMBH & Co. KG, Duisburg (DE)

( * ) Notice: Subject to any disclaimer, the term of this patent is extended or adjusted under 35 U.S.C. 154(b) by 206 days.

(21) Appl. No.: 15/774,145

(22) PCT Filed: Nov. 9, 2016

(86) PCT No.: PCT/EP2016/077169
§ 371 (c)(1),
(2) Date: May 7, 2018

(87) PCT Pub. No.: WO2017/081099
PCT Pub. Date: May 18, 2017

(65) Prior Publication Data
US 2018/0328834 A1    Nov. 15, 2018

(30) Foreign Application Priority Data

Nov. 9, 2015    (DE) .................. 10 2015 119 267

(51) Int. Cl.
*G01N 19/10* (2006.01)
*G01N 25/66* (2006.01)
(Continued)

(52) U.S. Cl.
CPC ............. *G01N 19/10* (2013.01); *G01N 25/66* (2013.01); *G01N 27/048* (2013.01); *G01N 33/442* (2013.01); *G01N 2291/021* (2013.01)

(58) Field of Classification Search
CPC ....... G01N 19/10; G01N 25/66; G01N 27/048
(Continued)

(56) References Cited

U.S. PATENT DOCUMENTS 3,861,054 A     1/1975  Stahl
5,082,486 A *   1/1992  Glogowski ............... C05F 3/00
                                                                71/9
(Continued)

FOREIGN PATENT DOCUMENTS

CN    101351704 A    1/2009
CN    103091366 A    5/2013
(Continued)

OTHER PUBLICATIONS

Office Action in corresponding Japanese Application No. 2018-543450 dated Jul. 13, 2020 (in Japanese and English Translation).

*Primary Examiner* — Nimeshkumar D Patel
*Assistant Examiner* — Jean F Morello
(74) *Attorney, Agent, or Firm* — Harness, Dickey & Pierce, P.L.C.

(57) ABSTRACT

The disclosure relates to an apparatus for determining the moisture of a sample comprising a solid mixture, comprising at least one sample chamber for receiving the sample, at least one sensor for measuring a characteristic of a gas mixture surrounding the sample and a determination device for determining the moisture of the sample from the at least one characteristic. According to the disclosure, provision is made for the apparatus to comprise an measurement chamber which may be evacuated and which, in terms of flow, is selectively separable from the at least one sample chamber or connectable to the sample chamber, wherein the at least one sensor is configured to measure the characteristic of the gas mixture in the measurement chamber. The disclosure (Continued)

furthermore relates to a corresponding method for determining the moisture of a sample comprising a solid mixture.

12 Claims, 3 Drawing Sheets

(51) Int. Cl.
*G01N 27/04* (2006.01)
*G01N 33/44* (2006.01)

(58) Field of Classification Search
USPC .................................................. 73/29.02
See application file for complete search history.

(56) References Cited

U.S. PATENT DOCUMENTS

| | | |
|---|---|---|
| 5,191,211 A | 3/1993 | Gorman, Jr. |
| 5,301,440 A * | 4/1994 | Shimizu .............. G01N 5/045 34/168 |
| 7,398,681 B2 * | 7/2008 | Norbeck ................. G01P 5/12 73/204.11 |
| 2005/0080311 A1 | 4/2005 | Hasenberg et al. |

FOREIGN PATENT DOCUMENTS

| | | |
|---|---|---|
| CN | 103163308 A | 6/2013 |
| CN | 203786069 U | 8/2014 |
| DE | 2247569 A1 | 5/1973 |
| DE | 155115 A1 | 5/1982 |
| DE | 4001928 C2 | 2/1994 |
| DE | 69217735 T2 | 9/1997 |
| EP | 0520472 A2 | 12/1992 |
| EP | 1096244 A2 | 5/2001 |
| EP | 1359403 A1 | 11/2003 |
| JP | S5694950 U | 7/1981 |
| JP | H054716 A | 1/1993 |
| JP | H0743269 A | 2/1995 |
| JP | 2001507799 A | 6/2001 |
| WO | WO-9728434 A1 | 8/1997 |

* cited by examiner

APPARATUS AND METHOD FOR DETERMINING THE MOISTURE OF A SAMPLE

CROSS-REFERENCE TO RELATED APPLICATIONS

This application is a National Stage of International Application No. PCT/EP2016/077169 filed on Nov. 9, 2016, and published in German as WO2017/081099 A1 on May 18, 2017. This application claims the priority to German Patent Application No. 10 2015 119 267.5, filed on Nov. 9, 2015. The entire disclosures of the above applications are incorporated herein by reference.

FIELD

The disclosure relates to an apparatus for determining the moisture content of a sample comprising a solid mixture, including (i) at least one sample chamber for receiving the sample, (ii) at least one sensor for measuring a characteristic of a gas mixture surrounding the sample, and (iii) a determination device for determining the moisture content of the sample from the at least one characteristic. The disclosure further relates to a corresponding method for determining the moisture content of a sample comprising a solid mixture.

BACKGROUND

This section provides background information related to the present disclosure which is not necessarily prior art.

Such an apparatus is known as an apparatus for determining the moisture content of bulk materials from DD 155 115 A1. In this apparatus, a space results, for example, in a screw conveyor for conveying the bulk material, in which the bulk material itself and a gas space above this bulk material are present. The apparatus comprises a temperature sensor as well as a dew point sensor which measure the characteristics temperature and dew point of the gas mixture present in the gas space. The output signals of these sensors are fed to a determination device for determining the moisture content by converting and linking the output signals under consideration of a dew point-temperature curve, which in turn outputs an output signal for display or for control. The accuracy of the determination of the moisture content of the bulk material described in this document is relatively low, not least because it is not waited until an equilibrium state is achieved in the water content between the gas and the solid mixture.

In order to determine the moisture content of such a sample comprising a solid mixture more accurately, methods and apparatuses based on other measuring principles are currently used. In the known measuring principles either a reagent or other consumable materials in the form of chemicals are used. These are partly toxic, harmful to health and/or easily flammable. In addition, they must be replaced after a few measurements. The used material must then be collected properly and disposed cost-intensively.

SUMMARY

This section provides a general summary of the disclosure, and is not a comprehensive disclosure of its full scope or all of its features.

It is the object of the disclosure to provide an apparatus and a corresponding method for determining the moisture content of a sample, which allow a rapid and accurate determination of the moisture content of samples without the use of consumable materials.

The object is achieved according to the disclosure by the features of the independent claims. Advantageous embodiments of the disclosure are specified in the dependent claims.

In the apparatus according to the disclosure for determining the moisture content of a sample comprising a solid mixture with the features mentioned in the preamble of claim 1, it is provided that the apparatus has a measuring chamber which can be evacuated and which is selectively fluidically disconnectable from and connectable to the at least one sample chamber, wherein the at least one sensor is configured to measure the characteristic of the gas mixture in the measuring chamber. The apparatus is preferably an apparatus for determining the moisture content of a bulk material sample or another sample consisting of a solid mixture.

The moisture content of the sample is determined by means of the apparatus as follows: First, the sample is introduced into the sample chamber and optionally prepared there in such a way that the gas mixture surrounding the sample is formed in the desired manner in the sample chamber.

Then, the sample chamber is fluidically connected to the previously evacuated measuring chamber so that a portion of the gas mixture surrounding the sample flows from the sample chamber into the measuring chamber, where the measurement of the at least one characteristic of the gas mixture takes place. Subsequently, the moisture content of the sample located in the measuring chamber is determined by means of the determination device from the at least one measured characteristic. By means of a subsequent fluidic connection of the evacuated measuring chamber to the sample chamber or one of the sample chambers, an expansion of the gas mixture from the sample chamber into the measuring chamber occurs, wherein the size ratio of the sample chamber to the measuring chamber is chosen so that the gas mixture which entered the measuring chamber is at an operating point on the dew point curve required for an accurate measurement. The evacuation results in a dew point temperature $T_{Taupunkt}$ of, for example, $-20°$ C. The volume of the interior of the measuring chamber is preferably approximately three liters. The sample chamber(s) usually has/have a significantly lower internal volume.

Advantageously, the apparatus has at least one shut-off fitting, such as a valve or a shutter, via which the at least one sample chamber can optionally be fluidically connected to the measuring chamber or disconnected from the measuring chamber.

According to a preferred embodiment of the disclosure, the apparatus comprises at least one heater for heating the sample in the at least one sample chamber. By heating, the sample is brought to a desired temperature, whereby the gas mixture surrounding the sample is formed in a well-defined manner. The heating temperature is preferably above $100°$ C., more preferably in the range of $200°$ C., such as $150°$ C.$\leq T_H \leq 250°$ C. The measuring chamber preferably has (at least at the time of measurement) a significantly lower temperature $T_M$, i.e. $T_M \ll T_H$, preferably room temperature. Typically, however, measuring temperatures $T_M$ of up to $60°$ C. are possible. The use of the measuring chamber and the sample chamber has the advantage that the sensor or the sensors need not be bakeable, since they are mounted in or at the unheated measuring chamber.

In principle, the measuring chamber can of course be evacuated by means of an external vacuum pump. However, according to a preferred embodiment of the disclosure, the apparatus has its own pump for selectively evacuating the measuring chamber. It is usually completely sufficient if the pump is able to evacuate/empty the measuring chamber into the rough vacuum range, i.e. into the range of a few hPa or mbar residual gas pressure (for example 10 hPa). The pump is preferably fluidically connected to the measuring chamber or disconnected from the measuring chamber via a shut-off fitting, such as a valve or a shutter.

According to a further preferred embodiment of the disclosure, a plurality of sample chambers are provided. In this embodiment, several samples can be heated in parallel and the corresponding characteristics can be measured with a relatively high measurement rate, i.e. high repetition rate of the measurements.

According to yet another preferred embodiment of the disclosure, a plurality of sensors are provided. These sensors preferably measure different characteristics. Advantageously, one of the sensors is a temperature sensor.

In general, a variety of possible sensors are available for use in said apparatus. For example, a coulometric P205 sensor or a hair hygrometer may be mentioned here. From the characteristics of these sensors the determination device can then determine the moisture content of the sample.

However, according to a preferred embodiment of the disclosure it is provided that the sensor or at least one of the sensors is a dew point sensor. Thus, an apparatus is obtained whose basic measurement principle has some similarity with the aforementioned measurement principle of DD 155 115 A1. By means of the mentioned additional measures, however, a much higher accuracy in the determination of the moisture content of the sample can be achieved.

In this embodiment of the disclosure it is provided in particular that the dew point sensor determines the dew point temperature by means of a capacitive sensor element. Such a sensor element may be a sensor element based on a metal ceramic or a polymer sensor element. The moisture dependent capacity and the temperature of the gas are measured in a calibration procedure.

Alternatively, it is provided that the dew point sensor comprises a dew point mirror as a sensor element. This can also be used as a reference element for the absolute moisture.

According to yet a preferred embodiment of the disclosure, the apparatus further comprises a measuring, control and/or regulating device which is connected signal technically to the at least one sensor and also forms the determination device. Preferably, the measuring, control and/or regulating device is also connected signal technically to the at least one heater and/or to the shut-off fitting or the shut-off fittings. By means of the measuring, control and/or regulating device the entire process of determining the moisture content is controlled or regulated and, at the end, the moisture content of the sample is determined from the measured characteristic or the measured characteristics.

According to a further preferred embodiment of the disclosure the apparatus further comprises at least one fluid circulation system in which the measuring chamber is fluidically interconnected. By means of this fluid circulation system, for example, the residual moisture of the measuring system can be evenly distributed.

Advantageously, it is provided in this embodiment that the at least one sample chamber is interconnectable selectively or interconnected permanently in the at least one fluid circulation system. By virtue of this measure the gas mixture surrounding the sample can be introduced into the measuring chamber rapidly and in a controlled manner.

In the method according to the disclosure for determining the moisture content of a sample which comprises a solid mixture, comprising the steps of:
  providing the sample in a sample chamber,
  measuring a characteristic of a gas mixture surrounding the sample, and
  determining the moisture content of the sample from the at least one characteristic,
it is provided that the measurement of the at least one characteristic of the gas mixture is carried out in a measuring chamber which is fluidically connected to the at least one sample chamber, whereas the gas mixture surrounding the sample is previously formed in the sample chamber which is fluidically separated from the measuring chamber. In order to achieve a well-defined formation of the gas mixture surrounding the sample in the sample chamber, the sample in the sample chamber is preferably heated to a predetermined temperature.

The disclosure will now be described by way of example with reference to the accompanying drawings based on preferred exemplary embodiments, wherein the features shown below, both individually and in combination, may represent an aspect of the disclosure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

In the drawing.

Corresponding reference numerals indicate corresponding parts throughout the several views of the drawings.

DETAILED DESCRIPTION

Example embodiments will now be described more fully with reference to the accompanying drawings.

Figure 1:
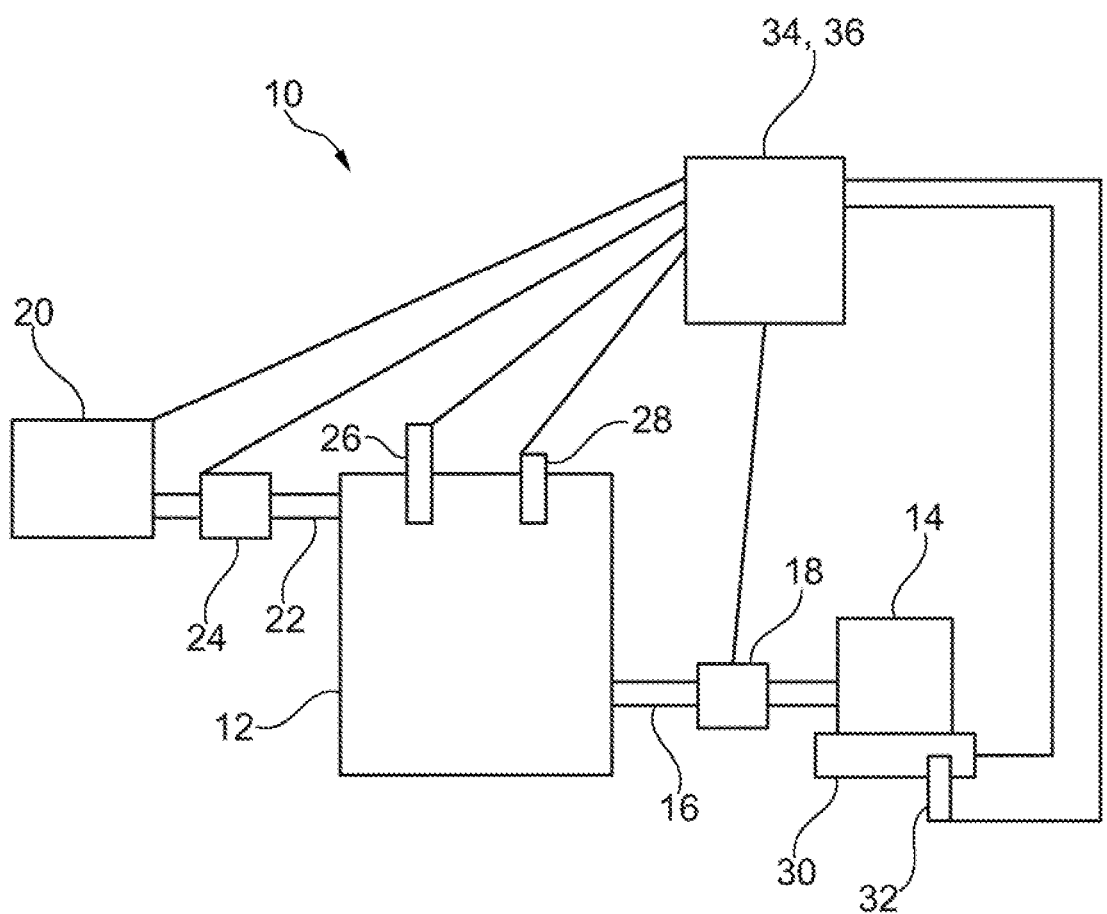
FIG. 1 shows a schematic representation of an apparatus for determining the moisture content of a sample comprising a solid mixture according to a preferred embodiment of the disclosure.

FIG. 1 shows an apparatus 10 for determining the moisture content of a sample comprising a solid mixture (sample not shown). The apparatus comprises as main components a measuring chamber 12 and a sample chamber 14 for receiving the sample. In general, the apparatus 10 may of course also comprise a plurality of such sample chambers 14, since, however, this is only a schematic representation, only one of these sample chambers 14 is shown. The volume of the interior of the measuring chamber 12 is preferably about 3 liters. The sample chamber(s) 14 usually has/have a significantly lower internal volume. The sample chamber 14 is fluidically connected to or in fluid communication with the measuring chamber 12 via a fluid connecting element 16 configured as a connecting tube. In the fluid connection element 16 a shut-off fitting 18 configured as a valve is connected. The apparatus further comprises a pump 20 for selectively evacuating the measuring chamber 12. The pump 20 is also fluidically connected to or in fluid communication with the measuring chamber 12 via a fluid connecting element 22 configured as a connecting tube. In this fluid connecting element 22, too, a shut-off fitting 24 configured as a valve is connected. In or at the measuring chamber 12 two sensors 26, 28 for measuring characteristics of a gas mixture located in the interior of the measuring chamber are mounted. One of the sensors is a dew point sensor 26, the other is a temperature sensor 28. In or at the sample chamber 14 a heater 30 for heating the chamber interior of the sample chamber 14, i.e. in particular the sample located therein, is mounted. At this heater (or alternatively at the sample chamber) a temperature sensor 32 is mounted, too. The apparatus 10 further comprises a measuring, control and/or regulating device 34 signal technically connected to the sensors 26, 28, the at least one heater 30 and the temperature sensor 32, the pump 20 and the shut-off fittings 18, 24. Said components 18, 20, 24, 30 can be driven by the measuring, control and/or regulating device 34 and said sensors and the measuring sensors 26, 28, 32 can be read out by the measuring, control and/or regulating device 34.

The following function is obtained:

The sample of known density to be measured is weighed and placed in the sample chamber 14. The fitting 18 between the sample chamber 14 and the measuring chamber 12 is closed. The heater 30 heats the sample chamber 14 and the sample placed therein to a desired temperature (e.g., about 200° C.). The valve 24 between the pump 20 and the measuring chamber 12 is opened and the measuring chamber 12 is pumped out by means of the pump 20. After a few minutes (depending on the size of the measuring chamber 12 and the power of the pump 20) a stable negative pressure and thus a corresponding dew point (i.e. a corresponding dew point temperature) has established in the measuring chamber 12 and the sample chamber 14 with the sample placed therein has reached a constant temperature for the measurement. Now the shut-off fitting 24 between the pump 20 and measuring chamber 12 is closed and then the sample chamber 14 is fluidically connected to the empty measuring chamber 12 by opening the shut-off fitting 18, so that a part of the gas mixture surrounding the sample flows from the sample chamber 14 into the measuring chamber 12 where the measurement of the characteristic of this gas mixture takes place. The water from the sample by means of the increased measurement temperature and the now reduced vapour pressure passes from the sample into the gas phase and now changes the dew point in the measuring chamber 12. After some time, the dew point is constant. Subsequently, the moisture of the sample placed in the measuring chamber 14 is determined from the measured characteristics by means of a determination device 36 formed by the measuring, control and/or regulating device 34. Based on the measured temperature and the dew point, it is possible to calculate the present amount of water per unit volume. Because the volumes in the measuring range and also the volume of the sample (via weight and density) are known, thus, the absolute amount of water present in the system can be calculated and compared with the original weight of the sample.

The use of separate measuring and sample chambers 12, 14 thus has the advantage that the sensor 10 or the sensors 26, 28 need not be bakeable, since they are indeed mounted in or at the unheated measuring chamber 12.

Now the fluid system of the apparatus 10 can be vented and the next sample can be measured. Since the sample chamber 14 is still hot, further sample chambers 14 can be connected to the measuring chamber 12 via connecting elements 16 and fittings 18. This makes it possible to schedule measurements in shorter intervals.

In order to increase the accuracy of the determination of the moisture content, the dew point is determined and the amount of water per unit volume is calculated prior to the actual measurement. The absolute amount of water, which is present in the air of the sample chamber 14 and the connected connecting element 16 is subtracted from the absolute amount of water in the system calculated at the end of the measurement.

By means of such an apparatus 10 for moisture determination, the moisture content in a solid mixture sample can be determined reliable down to a range of a few ppm without consumable materials. For example, a moisture determination with such an accuracy is desirable in processing solid mixture samples such as plastic granules.

The apparatus 10 shown is configured as a mobile moisture meter, indeed as a portable moisture meter.

FIGS. 2 to 5 show a further embodiment of the apparatus 10 for determining the moisture content of a sample comprising a solid mixture. Since the apparatus 10 shown in FIGS. 2 to 5 substantially corresponds to the apparatus 10 shown in FIG. 1, only the differences will be discussed here.

The apparatus shown in FIGS. 2 to 5 includes a fluid circulation system 38, in which the measuring chamber 12 and the pump 20 are fluidically permanently interconnected while the sample chamber 14 is selectively connectable in this fluid circulation system 38. For this purpose, the sample chamber 14 is connected in a line section 40, to which the fluid circulation system 38 comprises a parallel connected bypass 42. The sample chamber 14 is surrounded in the line section 40 by two shut-off fittings 44, 46 and the bypass has a shut-off fitting 48, too. By way of these fittings 44, 46, 48, optionally the line section 40 or the bypass 42 can be integrated into the circulation system 38. Here, these shut-off fittings 44, 46, 48 take over, inter alia, the function of the known shut-off fitting 24 of the apparatus shown in FIG. 1.

Furthermore, the apparatus 10 includes venting valves or other fittings 50, 52, via which the circulation system 38 can be vented. All fittings 18, 44, 46, 48, 50, 52 may for example be formed as valves and are preferably driven by the measuring, control and/or regulating device 34.

Figure 2:
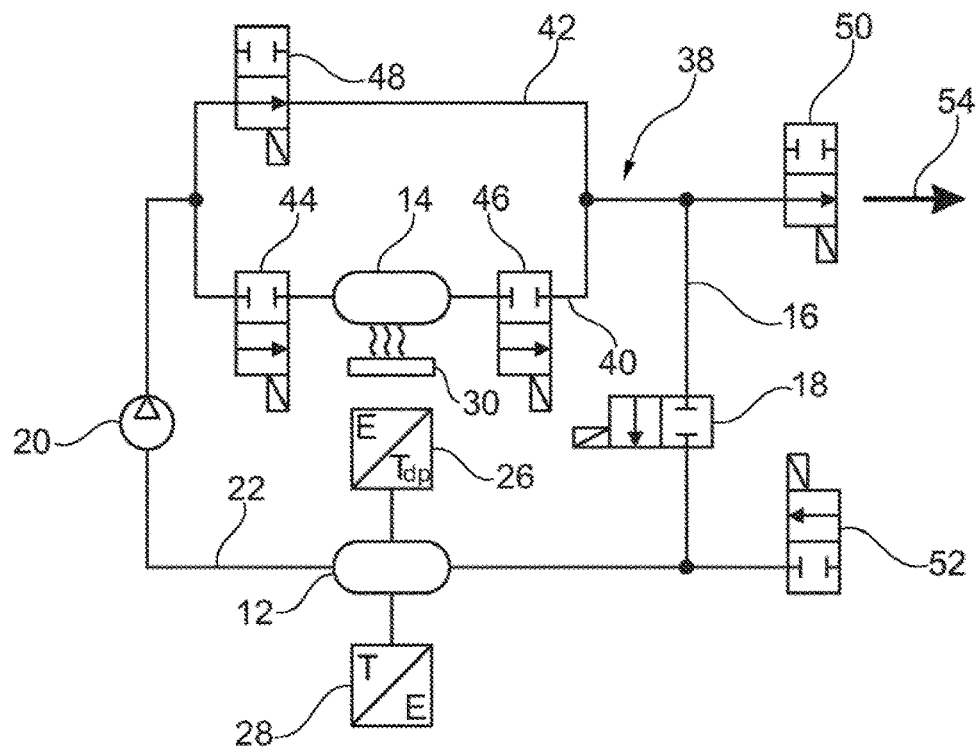
FIG. 2 shows the apparatus for determining the moisture content of a sample comprising a solid mixture in accordance with a further preferred embodiment of the disclosure during a pumping process.

In the determination of the moisture content by means of this embodiment of the apparatus 10 four successive phases for the measurement of the characteristic(s) are obtained:

FIG. 2 shows the first of these phases, namely the pumping process. During the pumping process, the measuring chamber 12 is evacuated by means of the pump 20. The sample chamber 14 is separated from the remainder of the circulation system 38 by means of the two shut-off fittings 44, 46 which are positioned directly upstream and downstream of the sample chamber 14. As a result, the baking process of the sample 5 can already be started in this phase. Via the bypass 42, the gas from the measuring chamber 12 can be pumped past the sample chamber 14 and is discharged via the fitting 50 into the environment (arrow 54).

The pumping process is terminated as soon as a preset dew point temperature (typically ≤−20° C.) or, if another sensor is selected, a predetermined negative pressure (typically approximately 10 mbar absolute) is reached.

Figure 3:
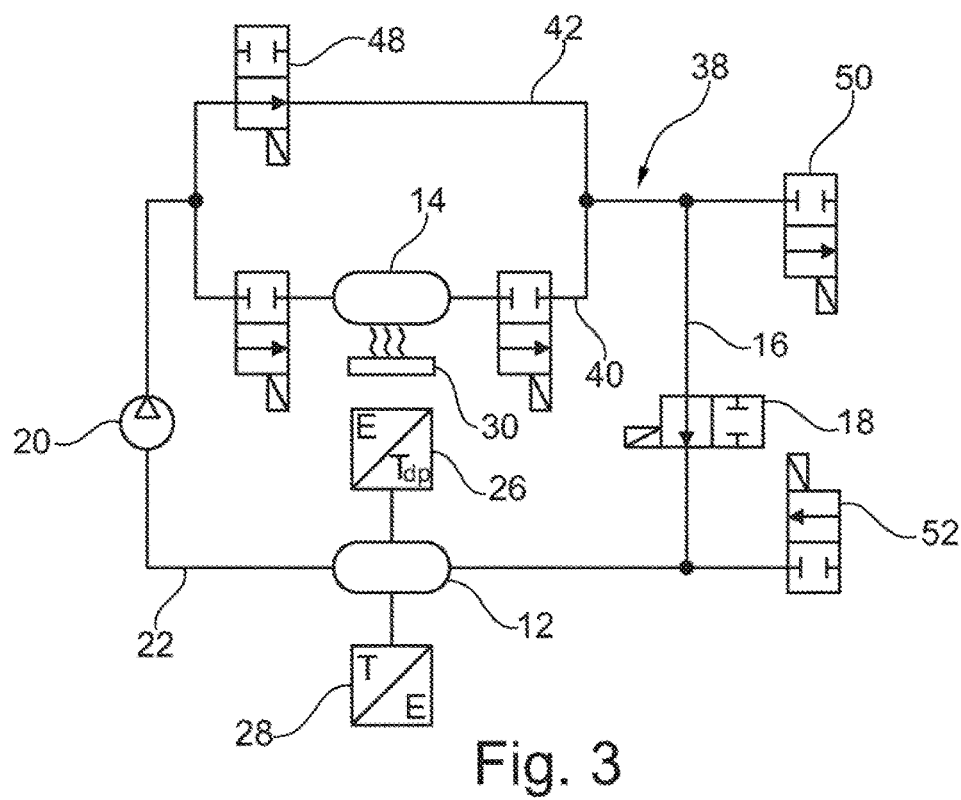
FIG. 3 shows the apparatus shown in FIG. 2 during a setting phase.

FIG. 3 shows the second of the phases, namely a setting phase. In the so-called setting phase, the circulation system 38 is sealed to the outside. The sample chamber 14 is further separated from the measuring chamber 12 and is still heated. In this phase, the pump 20 causes the residual gas in the system 38 to circulate. This circulation of the residual gas 15 firstly causes the residual moisture, which is still present in the system 38, to be evenly distributed. Secondly, the relatively slow dew point temperature sensor 26 and the relatively slow temperature sensor 28 reach an equilibrium state and thus a stable value. This is important because residual moisture remaining in the system is subtracted from the calculated moisture content of the sample at the end of the actual measuring process. The setting phase is terminated after a predetermined time (typically about 2 minutes).

Figure 4:
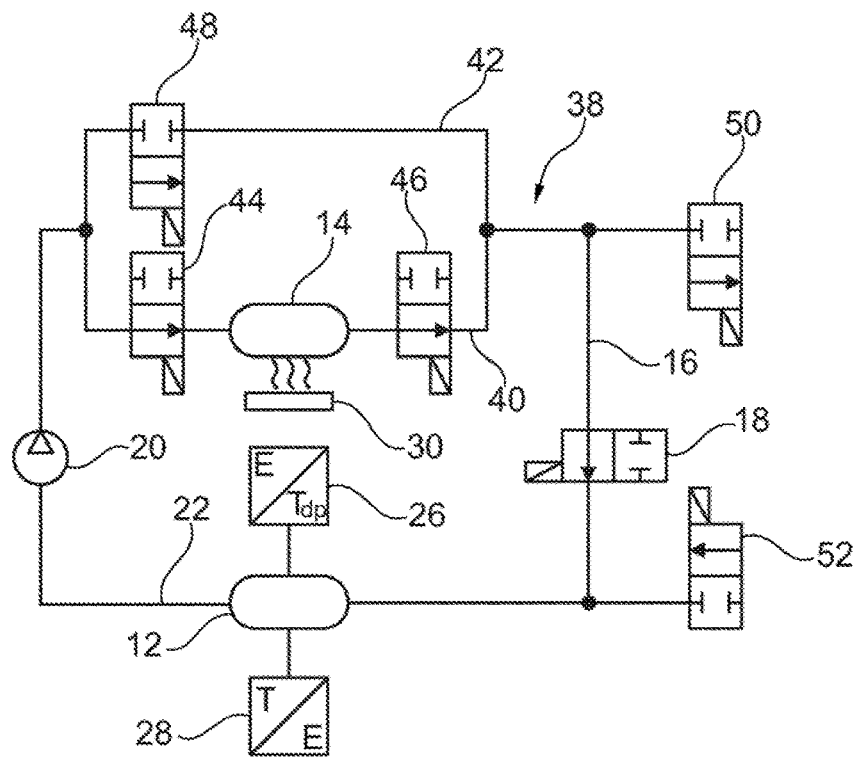
FIG. 4 shows the apparatus shown in FIGS. 2 and 3 during the measuring process.

FIG. 4 shows the third of the phases, namely the actual measuring phase. At the beginning of the measuring phase the bypass 42 is shut off by the shut-off fitting 48. The two shut-off fittings 44, 46 upstream and downstream of the sample chamber 14 are opened. The pump 20 causes the gas mixture surrounding the sample from the sample chamber 14 to circulate in the system 38, thus distributing the moisture from the sample rapidly and evenly throughout the system 38. The sample is still baked. The measuring phase or the measuring process can be terminated as soon as the value calculated from the dew point temperature and the gas temperature is constant for the amount of water (moisture) contained in the gas.

Figure 5:
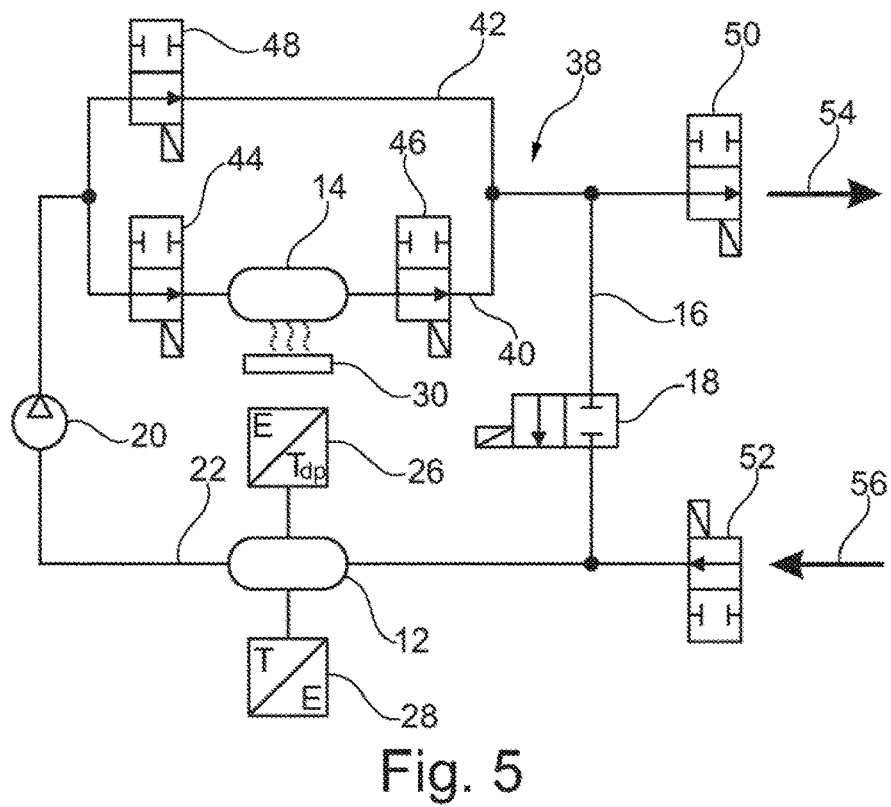
FIG. 5 shows the apparatus shown in FIGS. 2 to 4 during a rinsing process.

Finally, FIG. 5 shows the fourth of the phases, namely a rinsing process in preparation of a next measurement. During the rinsing process it is ensured that the moisture contained in the system 38 can leave the system 38. Both fittings 50, 52, which have separated the circulation system 38 from the surrounding atmosphere, are now opened. The pump 20 provides for a flow of ambient air through the entire system 38, in which now atmospheric pressure is present again (arrows 54, 56). Both the flow through the line section 40 with the sample chamber 14 and through the bypass 42 are provided. The sample chamber 14 is no longer heated. The air flow also ensures a faster cooling process.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

The invention claimed is:

1. An apparatus for determining the moisture content of a sample which comprises a solid mixture, comprising:
    at least one sample chamber for receiving the sample;
    at least one sensor for measuring a characteristic of a gas mixture surrounding the sample;
    a determination device for determining the moisture content of the sample from the at least one characteristic; and
    a measuring chamber wherein the at least one sensor is configured to measure the characteristic of the gas mixture in the measuring chamber;
    at least one shut-off fitting configured to selectively fluidically disconnect the measuring chamber from or connect the measuring chamber to the at least one sample chamber; and
    a pump for evacuating the measuring chamber.

2. The apparatus according to claim 1, further comprising at least one heater for heating the sample in the at least one sample chamber.

3. The apparatus according to claim 1, wherein the pump is adapted for evacuating the measuring chamber in the range of 10 hPa residual gas pressure or less.

4. The apparatus according to claim 1, wherein a plurality of sensors are provided.

5. The apparatus according to claim 1, wherein the sensor or at least one of the sensors is a dew point sensor.

6. The apparatus according to claim 5, wherein the dew point sensor determines the water vapour partial pressure by means of a capacitive sensor element.

7. The apparatus according to claim 1, further comprising a measuring, control and/or regulating apparatus which forms the determination device and is signal technically connected to the at least one sensor.

8. The apparatus according to claim 1, further comprising at least one fluid circulation system, in which the measuring chamber is fluidically interconnected.

9. The apparatus according to claim 8, wherein the at least one sample chamber, too, is selectively interconnectable or permanently interconnected in the at least one fluid circulation system.

10. The apparatus according to claim 1, wherein this apparatus is configured as a mobile moisture meter, in particular as a portable moisture meter.

11. A method for determining the moisture content of a sample which comprises a solid mixture, comprising the following steps:
    providing the sample in a sample chamber;
    evacuating a measuring chamber;
    measuring a characteristic of a gas mixture surrounding the sample, wherein the measurement is carried out in the measuring chamber after the measuring chamber being fluidically connected to the at least one sample chamber, wherein the gas mixture surrounding the sample forms beforehand in the sample chamber which is fluidically separated from the measuring chamber; and
    determining the moisture content of the sample from the at least one characteristic.

12. The method according to claim 11, wherein the residual gas pressure of the measuring chamber in the evacuated state is in the range of 10 hPa or less.

* * * * *